(12) United States Patent
Bedin

(10) Patent No.: US 10,823,732 B2
(45) Date of Patent: Nov. 3, 2020

(54) METHOD FOR THE IN VITRO PREDICTION OF THE PROBABILITY OF A PATIENT DEVELOPING SEVERE DENGUE, BASED ON A BLOOD SAMPLE

(71) Applicant: BIOMERIEUX, Marcy L'Etoile (FR)

(72) Inventor: Frederic Bedin, Lyons (FR)

(73) Assignee: BIOMERIEUX, Marcy l'Etoile (FR)

( * ) Notice: Subject to any disclaimer, the term of this patent is extended or adjusted under 35 U.S.C. 154(b) by 168 days.

(21) Appl. No.: 15/852,528

(22) Filed: Dec. 22, 2017

(65) Prior Publication Data

US 2018/0120316 A1 May 3, 2018

Related U.S. Application Data

(62) Division of application No. 14/364,456, filed as application No. PCT/FR2013/050143 on Jan. 23, 2013, now Pat. No. 9,863,948.

(30) Foreign Application Priority Data

Jan. 24, 2012 (FR) ..................... 12 50646

(51) Int. Cl.
 *G01N 33/82* (2006.01)
 *G01N 33/569* (2006.01)
 *G01N 33/68* (2006.01)

(52) U.S. Cl.
 CPC ... *G01N 33/56983* (2013.01); *G01N 33/6893* (2013.01); *G01N 33/82* (2013.01); *G01N 2333/185* (2013.01); *G01N 2333/4728* (2013.01); *G01N 2800/50* (2013.01); *G01N 2800/56* (2013.01); *Y02A 50/53* (2018.01)

(58) Field of Classification Search
 None
 See application file for complete search history.

(56) References Cited

U.S. PATENT DOCUMENTS

2010/0104587 A1    4/2010  Chavan et al.

FOREIGN PATENT DOCUMENTS

| WO | 2009145810 A2 | 12/2009 |
| WO | 2011092219 A1 | 8/2011 |
| WO | 2011127219 A1 | 10/2011 |
| WO | 2012178196 A2 | 12/2012 |

OTHER PUBLICATIONS

Bini et al. "Two-dimensional electrophoretic patterns of acute-phase human serum proteins in the course of bacterial and viral diseases", Eli,ctrophoresis 1996; 17: 612-616.*

(Continued)

*Primary Examiner* — Michelle S Horning
(74) *Attorney, Agent, or Firm* — Oliff PLC

(57) ABSTRACT

A kit for in vitro prediction of severe dengue includes a binding partner specific for leucine-rich alpha-2 glycoprotein, a binding partner specific for vitamin D-binding protein, and a binding partner specific for ferritin. The kit may further include at least one binding partner specific for a dengue virus protein wherein the dengue virus protein is the NS1 protein, the envelope protein, or the prM protein.

9 Claims, 5 Drawing Sheets

(56) References Cited

OTHER PUBLICATIONS

Chaiyaratana et al. "Serum Ferritin Levels in Children With Dengue Infection", SE Asian J. Trop. Med. Pub. Health, 2008; 39(5): 832-836.*

Albuquerque et al. "Two-Dimensional Difference Gel Electrophoresis (DiGE) Analysis of Plasmas from Dengue Fever Patients", J. Proteome Res. 2009; 8: 5431-5441.*

Albuquerque et al. "Two-Dimensional Difference Gel Electrophoresis (DiGE) Analysis of Plasmas From Dengue Fever Patients". Journal of Proteome Research, vol. 8, American Chemical Society., pp. 5431-5441, 2009.

Chaiyaratana et al. "Serum Ferritin Levels in Children With Dengue Infection". Southeast Asiain J Trop Med Public Health, vol. 39, No. 5., pp. 832-836, 2008.

Dec. 23, 2015 Office Action issued in U.S. Appl. No. 14/364,456.
Aug. 29, 2016 Office Action issued in U.S. Appl. No. 14/364,456.
Jan. 27, 2017 Office Action issued in U.S. Appl. No. 14/364,456.

Weivoda et al. "ELISA for Human Serum Leucine-Rich Alpha-2-Glycoprotein-1 Employing Cytochrome C as the Capturing Ligand". Journal of Immunological Methods, vol. 336., pp. 22-29, 2008.

Whitehorn and Simmons. "The Pathogensis of Dengue". Vaccine, vol. 29, pp. 7221-7228, 2011.

Srikiatkhachorn et al., "Markers of Dengue Disease Severity". Current Topics in Microbiology and Immunology, vol. 338., pp. 67-82, 2010.

Fragnoud et al. "Isotope Coded Protein Lableing Analysis of Plasma Specimens From Acute Severe Dengue Fever Patients". Proteome Science., vol. 10, 2012.

Halstead. "Dengue". The Lancet, vol. 370., pp. 1644-1652, 2007.

Leong et al. "The Pathology of Dengue Hemorrhagic Fever". Seminars in Diagnostic Pathology, vol. 24, No. 4., pp. 227-236, 2007.

Clyde et al. "Recent Advances in Deciphering Viral and Host Determinants of Dengue Virus Replication and Pathogenesis". Journal of Virology, American Society of Microbiology, vol. 80, No. 23., pp. 11418-11431, 2006.

Lottspeich et al. "ICPL Labeling Strategies for Proteome Research". Methods in Molecular Biology, vol. 753., pp. 55-64, 2011.

Pawitan. "Dengue Virus Infection: Predictors for Severe Dengue". Acta Med Indones-Indones J Intern Med, vol. 43, No. 2., pp. 129-135, 2011.

Mar. 20, 2013 International Search Report issued in International Patent Application No. PCT/FR2013/050143.

Mar. 20, 2013 Written Opinion issued in International Patent Application No. PCT/FR2013/050143.

\* cited by examiner

METHOD FOR THE IN VITRO PREDICTION OF THE PROBABILITY OF A PATIENT DEVELOPING SEVERE DENGUE, BASED ON A BLOOD SAMPLE

This is a Division of application Ser. No. 14/364,456, filed Jun. 11, 2014, which is a National Stage of PCT/FR2013/050143, filed Jan. 23, 2013, which claims priority to FR 1250646, filed Jan. 24, 2012. The disclosures of the prior applications are hereby incorporated by reference herein in their entireties.

The subject of the present invention is a method for the early prediction of severe dengue or hemorrhagic dengue using protein markers.

Over the past 30 years, dengue, a viral disease transmitted by urban hematophagous mosquitoes of the *Aedes* genus has worryingly spread throughout the world. It is currently an actual public health problem for more than one hundred countries located in the subtropical zone, particularly in the Pacific West, South America and South-East Asia zones. The emergence of the disease is largely due to the population explosion and to anarchic urbanization. Climatic abnormalities also have a not insignificant role. In this respect, dengue could emerge in the western regions of the world which until now have been spared the virus. Thus, *Aedes albopictus*, one of the vectors of the disease, has recently been found in the North of Italy and in the South of France. Most recently, autochthonous cases of dengue have been recorded in the South of France. It is estimated that close to three billion people are exposed to the risks of dengue. Close to one million hospitalizations are registered yearly and there have been thousands of deaths. Children are the main victims of the disease. The dengue virus is a single-stranded, positive-polarity enveloped RNA virus of the family Flaviviridae. The genome of the virus (11 000 nucleotides) encodes a polyprotein of approximately 3400 amino acids which undergoes co- and post-translational cleavage which results in structural proteins (C, prM, E) and non-structural proteins (NS1, NS2A, NS2B, NS3, NS4A, NS4B, NS5). There are 4 viral serotypes (DV1 to DV4), which can coexist in endemic zones. There is approximately 70% sequence homology between the various serotypes. Infection by a given serotype confers long-term immunity for this serotype. Cross-protection lasts only a few months: reinfection is therefore possible with a different serotype. The most common clinical manifestation ("conventional" Dengue Fever: DF) is a febrile state which lasts a few days, accompanied in particular by severe headaches, lumbago, and muscle and joint pain, which spontaneously regress without specific treatment after a few days. However, there are sometimes complications which result in hemorrhagic dengue (Dengue Hemorrhagic Fever: DHF). In this case, a transient increase in vascular permeability and leaking of plasma, responsible for thrombocytopenia and coagulopathy, are noted. In the most severe cases, the leaking of plasma can lead to deadly hypovolemic shock (Dengue Shock Syndrome: DSS) if the patient is not rapidly treated. Rare but deadly hepatic and neurological involvement is also associated with the severity of the disease. The mortality rate, which is variable according to epidemics, can reach 5% of established DHF cases. This rate can increase up to 20% without hospital care or appropriate treatments.

90% of DHF cases take place during a secondary infection by a heterologous serotype and 10% during a primary infection, usually in infants from 6 months to 1 year old. There are several factors which influence the severity of the infection, such as the host factors, the serotype and the genotype of the virus, the order of succession of the infecting viruses, the quality and the amount of cross-reaction antibodies and the CD4/CD8 response. The exact causes of the occurrence of DHF are, however, still not known with certainty. In a first hypothesis, it is the forces of selection exerted by the virus which result in the selection of a "super-virus". Studies have shown a correlation between viral load and severity of the disease. Studies have also implicated the E and NS1 viral proteins in the pathogenicity. The sequence of the infecting serotypes and the time between each infection are also important clinical determining factors.

A secondary infection with a different serotype is often associated with the severity of the disease, but is not a definite factor. It is the basis of the second hypothesis, the hypothesis of the facilitation of infection by low-affinity anti-dengue antibodies, which it has never been possible to confirm in vivo in the absence of an animal model. It is based on the presence of low-affinity neutralizing antibodies which facilitate the in vitro infection of macrophages via their immunoglobulin Fc receptor. The presence of the immune complexes moreover promotes complement activation.

The activation and excessive proliferation of memory CD4 and CD8+ T lymphocytes is thought to lead to the increased production of cytokines and of cell mediators. The concomitance of these various elements could be responsible for the pathogenicity. While the demonstration of the key role of lymphocyte activation and of mediator secretion in the physiopathology is quite well accepted, it is very difficult to show a clear correlation with the occurrence of DHF.

Genetic factors probably play a role since several studies have shown the either protective or pathogenic role of certain HLA class 1 alleles. However, the results are quite contradictory and vary depending on the origin of the samples.

Up until now, no specific determining factor for virulence has been demonstrated with certainty. Furthermore, since there is no vaccine against the dengue virus, the only treatments available are symptomatic treatments. Consequently, it is important to be able to monitor epidemics and to predict severe cases for appropriate hospital treatment [1, 2, 3].

The methods currently used to diagnose dengue do not make it possible to predict the development of severe dengue. At the very most, the serological methods make it possible to distinguish between primary and secondary infections and the molecular methods make it possible to detect the virus and to carry out serotyping.

The present invention provides a solution to the problems presented above by means of a method which allows both early and specific detection of proteins in a blood sample making it possible to predict severe dengue cases (DHF and/or DSS). Indeed, the applicant has found that proteins are quantitatively more abundant or overexpressed in severe dengue cases in comparison with the amount or expression thereof in conventional dengue cases, in blood samples corresponding to whole blood, serum or plasma. Quite particularly, they have shown for the first time and totally unexpectedly that leucine-rich alpha-2 glycoprotein (LRG) is overexpressed in the case of DHFs and that it therefore constitutes a marker for predicting severe dengue.

Thus, a subject of the present invention is a method for the in vitro prediction of the probability of a patient developing severe dengue based on a blood sample, which involves:

a) determining the quantity of at least one marker which is leucine-rich alpha-2 glycoprotein in said blood sample, b) comparing the quantity of leucine-rich alpha-2 glycoprotein determined in step a) with a reference quantity of said marker obtained from a group of individuals who have been diagnosed with non-severe dengue, wherein, if the quantity of leucine-rich alpha-2 glycoprotein determined in step a) is greater than the reference quantity established in step b), it is predicted that the patient will develop severe dengue.

In one embodiment of the method of the invention, in step a), the quantity of at least one other marker chosen from vitamin D-binding protein and ferritin is also determined in the blood sample and, in step b), the quantity of said other marker of step a) is compared with a reference quantity of said other marker obtained from a group of individuals who have been diagnosed with non-severe dengue and, if the quantity of said at least one other marker determined in step a) is greater than the reference quantity established in step b), it is predicted that the patient will develop severe dengue.

In another embodiment of the method of the invention, in step a), the quantity of at least two other markers chosen from vitamin D-binding protein and ferritin is also determined in the blood sample and, in step b), the quantity of each of the two other markers of step a) is compared with a reference quantity for each of said other markers obtained from a group of individuals who have been diagnosed with non-severe dengue and, if the quantity of each of the other markers determined in step a) is greater than the reference quantity of each of the markers established in step b), it is predicted that the patient will develop severe dengue.

A subject of the invention is also the use, for the in vitro prediction of severe dengue in a patient, of:

leucine-rich alpha-2 glycoprotein as a marker of the pathological condition, leucine-rich alpha-2 glycoprotein and vitamin D-binding protein or ferritin as markers of the pathological condition, and leucine-rich alpha-2 glycoprotein and vitamin D-binding protein and ferritin as markers of the pathological condition.

The invention also relates to a kit for the in vitro prediction of severe dengue, comprising:

a binding partner of leucine-rich alpha-2 glycoprotein, a binding partner of vitamin D-binding protein, and a binding partner of ferritin, plus optionally at least one binding partner of at least one dengue virus protein chosen from the NS1 protein, the envelope protein and the prM protein.

Definitions

The term "blood sample" is intended to mean whole blood, serum and plasma.

The term "binding partner" is intended to mean, for example, receptors, antibodies, antibody fragments, antibody analogs and any other ligand capable of binding to a protein.

The binding-partner antibodies are, for example, either polyclonal antibodies or monoclonal antibodies.

The polyclonal antibodies may be obtained by immunization of an animal with the appropriate immunogen, followed by recovery of the desired antibodies in purified form, by taking the serum of said animal, and separation of said antibodies from the other serum constituents, in particular by affinity chromatography on a column to which is bound an antigen specifically recognized by the antibodies.

The monoclonal antibodies can be obtained by the hybridoma technique, the general principle of which is summarized below.

Firstly, an animal, generally a mouse, is immunized with the appropriate immunogen, and the B lymphocytes of said animal are then capable of producing antibodies against this antigen. These antibody-producing lymphocytes are then fused with "immortal" myeloma cells (murine in the example) so as to give rise to hybridomas. Using the heterogeneous mixture of cells thus obtained, a selection of the cells capable of producing a particular antibody and of multiplying indefinitely is then carried out. Each hybridoma is multiplied in the form of a clone, each resulting in the production of a monoclonal antibody of which the recognition properties with respect to the protein may be tested, for example, by ELISA, by one-dimensional or two-dimensional Western blotting, by immunofluorescence, or by means of a biosensor. The monoclonal antibodies thus selected are subsequently purified, in particular according to the affinity chromatography technique described above.

The monoclonal antibodies may also be recombinant antibodies obtained by genetic engineering, using techniques well known to those skilled in the art.

The term "antibody analogs" is intended to mean biological and/or chemical compounds which have the same binding capacities as the antibodies or antibody fragments or similar binding capacities.

In particular, the antibody analogs include small proteins which, like antibodies, are capable of binding to a biological target thus making it possible to detect it, to capture it or quite simply to target it within an organism or within a biological sample. The fields of application of these antibody analogs are virtually as vast as those of antibodies. By way of example, mention may be made of the Nanofitins™, which are small proteins sold by the company Affilogic.

The binding partners specific for the desired protein can be used as a capture reagent, as a detection reagent or as capture and detection reagents.

The visualization of the immunological reactions, i.e. the protein/binding partner binding, can be carried out by any means of detection, via labeling, of the binding partner.

The term "labeling" is intended to mean the binding of a label reagent capable of generating a detectable signal, i.e. a compound, a substance or a particle which can be detected by visual, fluorescent or instrumental means.

A nonlimiting list of these label reagents consists of:
metal or alloy particles, such as colloidal gold particles,
polymer particles, such as colored latex particles,
magnetic particles,
fluorescent particles,
chemoluminescent molecules.

By way of example of immunological tests as defined above, mention may be made of "sandwich" and "competition" methods.

FIGURES

The figures illustrate the confirmation and the validation of the ICPL results for each candidate marker selected by means of a quantitative ELISA assay carried out on individual samples from patients taken during the acute phase of the disease (DF and DHF patients), before defervescence. In all cases, the reading is carried out at an optical density (OD) of 450 nm. The results were obtained on the Tahitian samples, on the Columbian samples and on a mixture of the two. The calculated mean is represented by a horizontal line (GraphPad Prism software). The values correspond to two independent assays carried out in duplicate.

EXAMPLES

Figure 1:
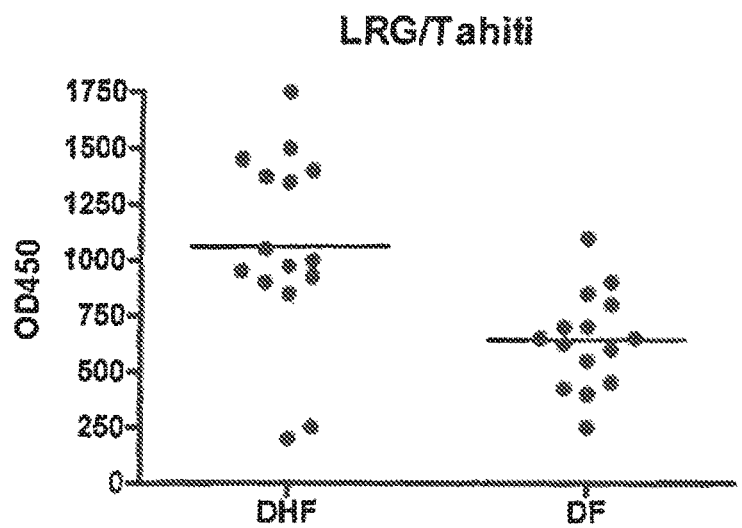
FIG. 1 illustrates the results obtained for the quantitative assaying by means of an ELISA assay of the LRG marker on plasma samples from Tahitian patients.

Example 1: Sample Selection and Pretreatment 10 samples of plasma from patients originating from a retrospective study carried out by the Institut Louis Malardé, Papeete, Tahiti (French Polynesia) were selected, among which were 5 samples from patients having developed conventional dengue (DF) and 5 samples from patients having developed sever dengue (DHF), which were grouped together, thus constituting a DF pool and a DHF pool. The selection criteria were homogeneity in terms of age (11 years+/−1 year) and date on which the sample was taken after the appearance of the symptoms (4 days+/−1 day). This is because a marker which is predictive of the severe forms must be detectable after the appearance of the symptoms of the infection by the dengue virus (appearance of the fever), but before defervescence, which corresponds to the passage to the severe forms. The male/female proportion was identical (ratio=3/2). In the two pools, the patients were suffering from a secondary infection by a virus of serotype 2 (DV2). The specific immunoglobulin M titer was low or undetectable. The viral load was detectable in all cases. For each pool, 40 µl of each of the 5 samples were mixed, thereby constituting 2 groups of DF and DHF samples having a total volume of 200 µl.

In order to exclude the most abundantly represented proteins (albumin, immunoglobulin, transferin, fibrinogen, alpha-2 microglobulin, haptoglobulin, etc.), the presence of which can mask the weakly represented proteins and therefore create a bias in terms of the choice of proteins of interest, a depletion was carried out by means of the Proteoprep20™ kit sold by Sigma-Aldrich (USA). This kit enables a depletion of the 20 most abundant plasma proteins. The protocol used was the one recommended by the supplier. At the end of this immunodepletion, 2 groups of samples were available: a depleted DF pool and a depleted DHF pool. The pools were checked on a bis-tris 4-12% polyacrylamide gel (InVitrogen™, UK) in order to validate the depletion step.

Example 2: Identification of the Specific Proteins of Each Pool

After reduction and alkylation of the cysteine residues, each pool was differentially analyzed using the ICPL (Isotope Coded Labeled Protein) technique, developed by the company Brucker™. This technique allows differential studies by labeling of the samples to be compared [4]. The proteins are specifically labeled on their lysines with a reagent containing $^{12}C$: light isotope for the DF pool, and with a reagent containing $^{13}C$: heavy isotope for the DHF pool. This results in a difference in mass, provided by the two isotopes. After mixing of the two differently labeled samples, the proteins are fractionated by one-dimensional polyacrylamide gel electrophoresis. The gel is then fractionated into 20 bands. These bands are hydrolyzed using trypsin. The proteins of each hydrolyzate are separated by NANOLC liquid chromatography, ionized by electrospray ionization and identified by ion trap mass spectrometry (2 deposits per band). The WARPLC software enables automatic selection of the differential peaks to be identified by MS/MS. The table below lists the candidate proteins identified at the end of this study. The protein differential identified by ICPL on the DF and DHF pools is given in detail. The table indicates the nature of the protein and the heavy isotope/light isotope signal ratio (Avg). For certain proteins, the heavy/light ratio is in favor of a strong proportion of "light" signal (Avg.<0.5), therefore each protein is potentially a marker specific for non-severe, conventional dengue (DF). For other proteins, the heavy/light ratio is in favor of a strong proportion of "heavy" signal (Avg.>1.6) and each protein is potentially a marker specific for severe dengue. The inventors have selected proteins as potential marker candidates for DF or DHF. They are:

peroxyredoxin-2,
vitamin D-binding protein,
afamin,
leucine-rich alpha-2 glycoprotein,
galectin-3-binding protein,
C-reactive protein,
ferritin light chain.

Haptoglobin was excluded since it is part of the majority of plasma proteins and should normally have been removed by the Proteoprep20 column. The C7 complement protein was also not retained owing to its ubiquitous nature.

TABLE 1

Proteins identified by ICPL on the Tahiti plasma pools

| Protein | Accession | H/L | Avg | Max. Avg | Max. cv |
|---|---|---|---|---|---|
| Peroxyredoxin-2 | P322119 | 9 | 0.33 | 0.08 | 41.55 |
| Haptoglobin | P00738 | 13 | 0.43 | 0.150 | 45.03 |
| complement C7 | P10643 | 8 | 0.48 | 0.030 | 12.026 |
| Apolipoprotein A | P06727 | 3 | 0.68 | 0.310 | 48.72 |
| Fibrinogen alpha chain | P02671 | 4 | 0.79 | 0.030 | 5.16 |
| Apolipoprotein E | P02649 | 6 | 0.8 | 0.0140 | 26.45 |
| Amyloid A protein | P02735 | 7 | 0.92 | 0.070 | 16.59 |
| Fibrinogen beta chain | P002765 | 9 | 0.93 | 0.050 | 10.68 |

TABLE 1-continued

Proteins identified by ICPL on the Tahiti plasma pools

| Protein | Accession | H/L | Avg | Max. Avg | Max. cv |
|---|---|---|---|---|---|
| Inter-alpha-trypsin inhibitor H1 | P19827 | 7 | 0.94 | 0.230 | 37.76 |
| Complement factor H-related protein 1 | Q03591 | 14 | 0.95 | 0.140 | 21.99 |
| Inter-alpha-trypsin inhibitor H2 | P19823 | 15 | 0.98 | 0.27 | 39.51 |
| Fibrinogen gamma chain | P02679 | 3 | 0.99 | 0.01 | 1.87 |
| Vitronectin | P04004 | 2 | 1 | 0.1 | 14.28 |
| Complement factor B | P00751 | 8 | 1.06 | 0.1 | 17.54 |
| Complement C4 | POCOL4 | 3 | 1.06 | 0.304 | 9.24 |
| Albumin | P02768 | 27 | 1.09 | 0.18 | 25.57 |
| alpha-2 antiplasmin | P08697 | 5 | 1.18 | 0.203 | 4.13 |
| Antithrombin III | P01008 | 16 | 1.23 | 0.13 | 24.64 |
| Apolipoprotein A1 | P02647 | 74 | 1.24 | 0.21 | 69.85 |
| Retinol-binding protein | P02753 | 5 | 1.24 | 0.13 | 13.3 |
| Prothrombin | P00734 | 4 | 1.26 | 0.15 | 14.18 |
| Complement factor 1 | P05156 | 3 | 1.27 | 0.02 | 2.96 |
| Beta-microglobulin | P61769 | 3 | 1.27 | 0.05 | 4.94 |
| Ig alpha-1 chain C | P01876 | 2 | 1.27 | 0.042 | 0.18 |
| Hemopexin | P02790 | 28 | 1.27 | 0.14 | 37.26 |
| Alpha 1B glycoprotein | P04217 | 4 | 1.28 | 0.08 | 9.49 |
| Amyloid A4 protein | P35542 | 6 | 1.29 | 0.14 | 16.83 |
| Kininogen 1 | P01042 | 3 | 1.3 | 0.346 | 11.97 |
| IgMu chain C | P01871 | 2 | 1.3 | 0.057 | 0.32 |
| Cysteine-rich protein 2 | P16562 | 2 | 1.3 | 0.212 | 4.5 |
| Zinc-alpha2-glycoprotein | P25311 | 7 | 1.3 | 0.12 | 19.75 |
| Extracellular matrix protein | Q16610 | 2 | 1.32 | 0.057 | 0.32 |
| Pigmentary epithelial factor | P36955 | 3 | 1.35 | 0.1 | 15.72 |
| Complement C3 | P01024 | 7 | 1.37 | 0.19 | 25.84 |
| Attractin | O75882 | 4 | 1.38 | 0.2 | 22.01 |
| Complement factor H-related protein 2 | P36980 | 2 | 1.41 | 1.443 | 208.08 |
| Apolipoprotein B-100 | P04114 | 6 | 1.43 | 0.26 | 32.29 |
| Complement factor H | P08603 | 24 | 1.46 | 0.41 | 29.06 |
| Alpha1-antichemoptrypsin | P01011 | 6 | 1.48 | 0.2 | 21.84 |
| Angiotensinogen | P01019 | 4 | 1.54 | 0.25 | 22.71 |
| Histidine-rich glycoprotein | P04196 | 2 | 1.54 | 1.259 | 158.42 |
| Inter-alpha-trypsin inhibitor chain H4 | Q14624 | 5 | 1.54 | 0.09 | 7.18 |
| Serum amyloid P component | P02743 | 15 | 1.56 | 0.23 | 29.2 |
| Clusterin | P10909 | 7 | 1.57 | 0.25 | 29.73 |
| Vitamin D-binding protein | P02774 | 13 | 1.63 | 0.75 | 64.18 |
| Afamin | P43652 | 6 | 1.85 | 0.34 | 29.98 |
| Fibronectin | P02751 | 9 | 1.99 | 0.28 | 27.97 |
| Leucine-rich alpha-2 glycoprotein | P02750 | 2 | 2.26 | 0.884 | 78.12 |
| Galectin-3-binding protein | Q08380 | 0 | 2.66 | 0.26 | 10.97 |
| C-reactive protein | P02741 | 3 | 3.87 | 0.365 | 13.29 |
| Ferritin light chain | P02792 | 5 | 5.75 | 1.7 | 39.29 |

Example 3: Confirmation ELISA

Materials and Methods:

In order to confirm and validate the ICPL results, each candidate marker was tested by quantitative ELISA on individual samples. These samples were samples from patients having developed either "conventional" dengue or severe dengue and were taken during the acute phase of the disease (viremic phase). All the patients had secondary dengue. Only serotypes 1, 2 and 3 were represented (not serotype 4). These samples originated from the Institut Louis Malardé (Tahiti, French Polynesia) or originated from the Universidad Industrial de Santander (Bucaramanga, Colombia). The latter were part of a retrospective study carried out in agreement with the local ethics committee.

The quantitative ELISAs were carried out using commercial kits, according to the instructions supplied by the manufacturers. All the samples were tested twice and in duplicate. The list of commercial kits used is the following:

for vitamin D-binding protein: the HUMAN DBP™ kit, USCN Life (Wuhan, China), for afamin: the AFM™ kit, USCN life (Wuhan, China), for leucine-rich alpha-2 glycoprotein: the HUMAN-LRG™ kit, IBL International (Hamburg, Germany), for galectin-3-binding protein: the MAC-2 BP™ kit, IBL International (Hamburg, Germany), for C-reactive protein: the high-sensitive CRP ELISA™ kit, IBL International (Hamburg, Germany), for ferritin light chain: the FERRITIN™ kit, IBL International (Hamburg, Germany).

For peroxyredoxin-2, the absence of commercial tests necessitated the development of an ELISA. To do this, anti-peroxyredoxin-2 polyclonal antibodies, obtained either in rabbits (SAB2101878, Sigma-Aldrich USA) or in goats (SAB2500777, Sigma-Aldrich), were used. These antibodies are diluted to 2 µg/ml in a Tris-maleate buffer, pH 6.2, and used at the bottom of the plate. After washing, the plates sensitized with these antibodies are saturated for 1 h at 37° C. with a PBS-0.5% gelatin buffer. The sample to be tested is then added at various dilutions in PBS-0.05% Tween 20-0.1% gelatin and incubated for 1 h at 37° C. After three washes with PBS-0.5% Tween20, an anti-peroxyredoxin-2 mouse monoclonal antibody is added (WHO007001M1, Sigma-Aldrich; dilution: 1 µg/ml) and incubated for 1 h at 37° C. The visualization is carried out using the one-step NBT-BCIP™ kit (Thermo Scientific, USA) in the presence of an alkaline phosphatase-labeled anti-species conjugate diluted to 0.1 µg/ml (Jackson, USA).

Figure 2:
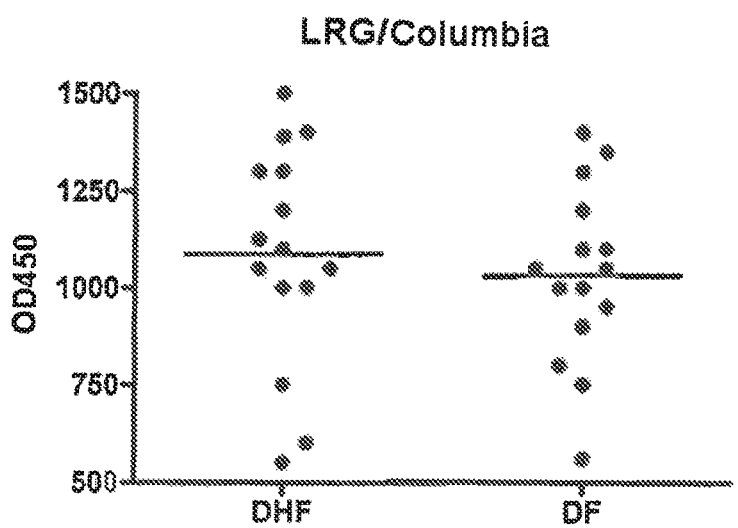
FIG. 2 illustrates the results obtained for the quantitative assaying by means of an ELISA assay of the LRG marker on serum samples from Columbian patients.
Figure 3:
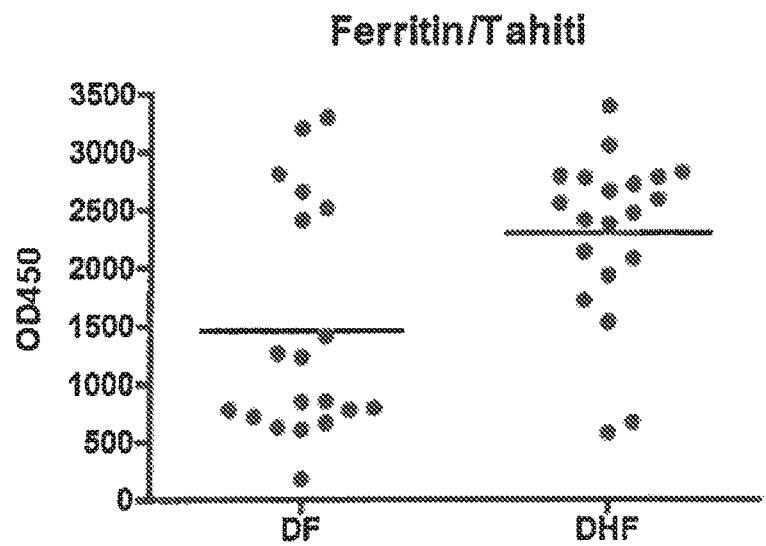
FIG. 3 illustrates the results obtained for the quantitative assaying by means of an ELISA assay of the ferritin marker on plasma samples from Tahitian patients.
Figure 4:
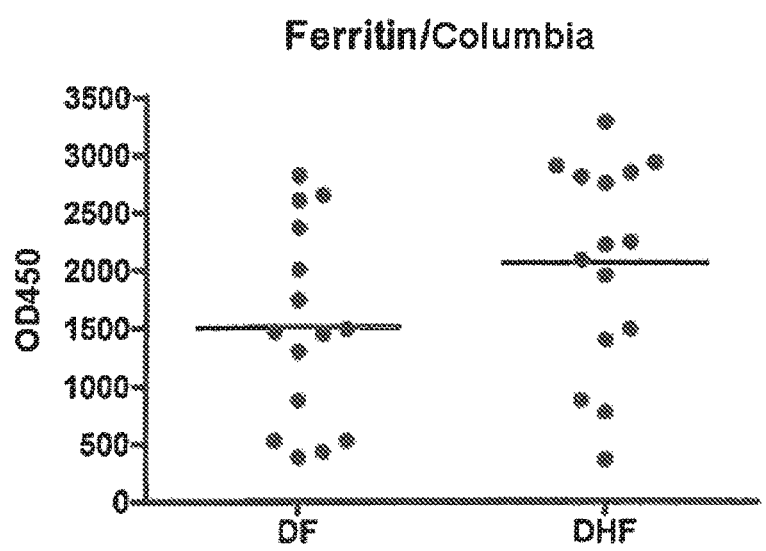
FIG. 4 illustrates the results obtained for the quantitative assaying by means of an ELISA assay of the ferritin marker on serum samples from Columbian patients.
Figure 5:
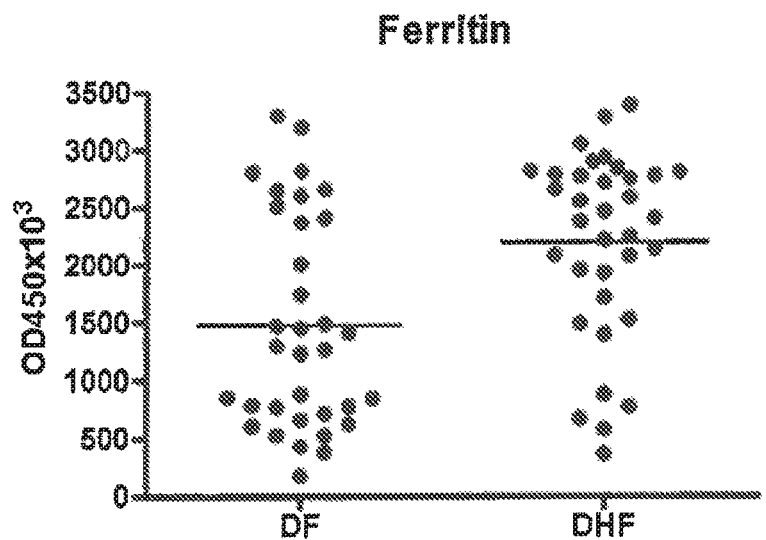
FIG. 5 illustrates the results obtained for the quantitative assaying by means of an ELISA assay of the ferritin marker on a mixture of plasmas of Tahitian origin and of sera of Columbian origin.
Figure 6:
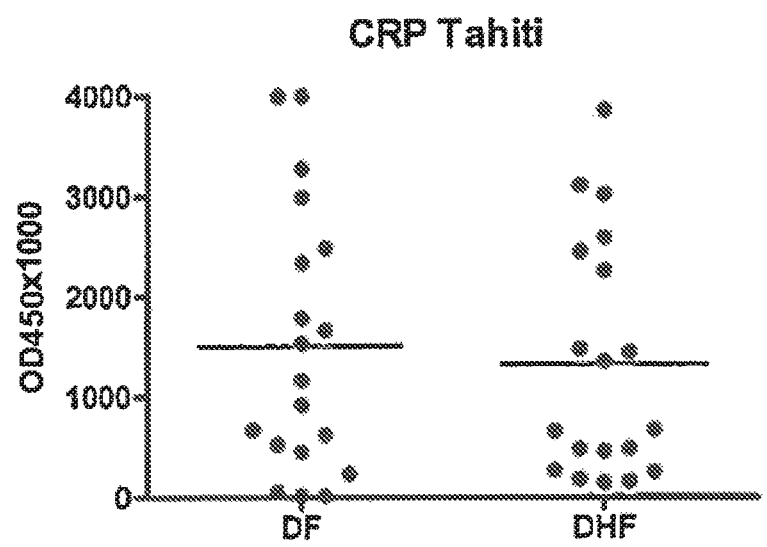
FIG. 6 illustrates the results obtained for the quantitative assaying by means of an ELISA assay of the CRP marker on plasma samples originating from Tahitian patients.
Figure 7:
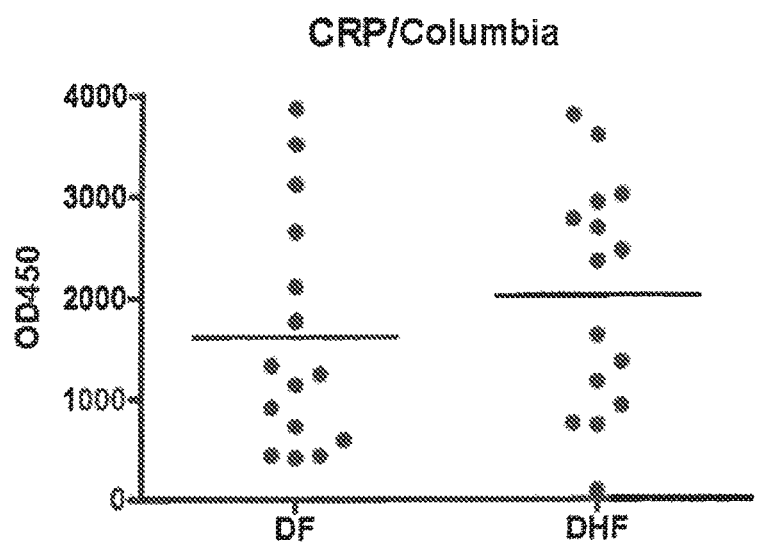
FIG. 7 illustrates the results obtained for the quantitative assaying by means of an ELISA assay of the CRP marker on serum samples originating from Columbian patients.
Figure 8:
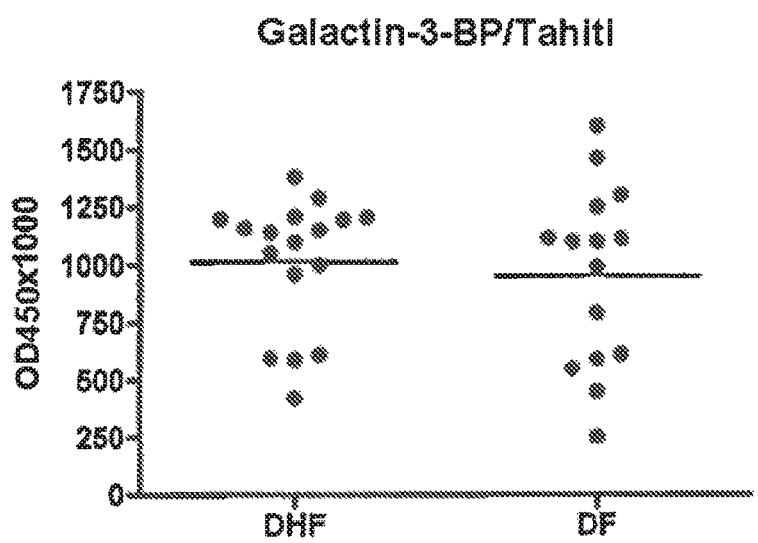
FIG. 8 illustrates the results obtained for the quantitative assaying by means of an ELISA assay of the galectin-3-binding protein marker on plasma samples originating from Tahitian patients.
Figure 9:
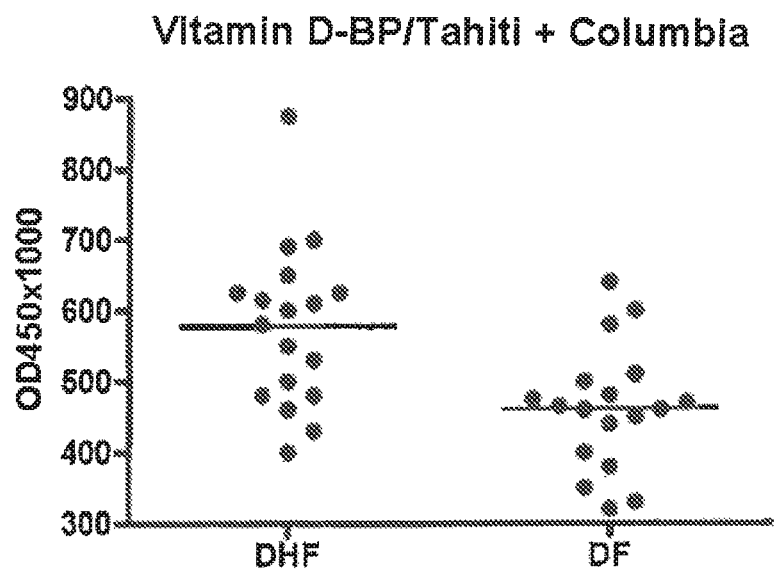
FIG. 9 illustrates the results obtained for the quantitative assaying by means of an ELISA assay of the vitamin D-binding protein marker on a mixture of plasmas of Tahitian origin and of sera of Columbian origin.
Figure 10:
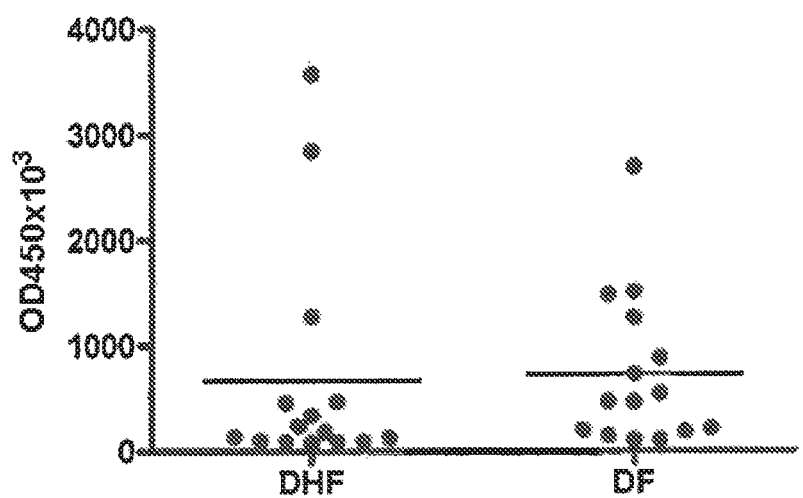
FIG. 10 illustrates the results obtained for the quantitative assaying by means of an ELISA assay of the Afamin marker on plasma samples from Tahitian patients.

Results:

The results are given in detail in FIGS. 1 to 10 and in table 2 which follows:

TABLE 2 p values for the various candidate markers tested on Tahitian and/or Columbian samples

| | P Value | | |
|---|---|---|---|
| Markers | Colombia (serum) | Tahiti (plasma) | Mixture |
| Vitamin D-BP | 0.01 | 0.008 | 0.0017 |
| LRG | 0.1 | 0.015 | 0.072 |
| Ferritin | 0.07 | 0.005 | 0.0018 |
| CRP | 0.1 | 0.4 | NT |
| Afamin | NT | 0.7 | NT |
| Peroxyredoxin-2 | NT | 0.4 | 0.38 |
| G3BP | NT | 0.6 | NT |

The differences obtained between the two populations (DF/DHF) were validated by means of a statistical test (unpaired t-test, Prism V4.03 Graphpad software). The significance threshold $p<0.05$ was retained, corresponding to a confidence interval of 95%. The results show a significantly greater quantity in the DHF samples for the following proteins: vitamin D-binding protein (vitamin D-BP), leucine-rich glycoprotein (LRG) and ferritin, which makes them very advantageous markers, taken individually or in combination, for predicting severe dengue on the basis of blood samples as soon as the first symptoms of dengue appear.

LITERATURE REFERENCES

1. S B Halstead. The lancet 2007; 370: 1644-52
2. A S Leong et al. Semin. Diagn. Pathol. 2007; 24(4):227-236
3. K. Clyde et al. J. Virol. 2006; 23: 11418-11431

4. Lottspeich F, Kellermann J. ICPL labeling strategies for proteome research. *Methods Mol Biol.* 2011; 753:55-64.

The invention claimed is:

1. A kit for in vitro prediction of severe dengue, comprising:
   an antibody specific for leucine-rich alpha-2 glycoprotein;
   an antibody specific for vitamin D-binding protein; and
   an antibody specific for ferritin.

2. The kit as claimed in claim 1, further comprising at least one binding partner specific for a dengue virus protein wherein the dengue virus protein is the NS1 protein, the envelope protein, or the prM protein.

3. The kit as claimed in claim 1, wherein at least one antibody is labeled with a label capable of generating a detectable signal.

4. The kit as claimed in claim 3, wherein the detectable signal is visually detectable.

5. The kit as claimed in claim 3, wherein the detectable signal is a fluorescent signal.

6. The kit as claimed in claim 3, wherein the detectable signal is detectable by an instrument.

7. The kit as claimed in claim 1, wherein the antibodies are components of an immunological assay.

8. The kit as claimed in claim 7, wherein the immunological assay is a sandwich assay or competition assay.

9. The kit as claimed in claim 2, wherein the binding partner specific for the dengue virus protein is an antibody.

\* \* \* \* \*